United States Patent
Martin

(10) Patent No.: US 11,666,553 B2
(45) Date of Patent: *Jun. 6, 2023

(54) METHOD OF REDUCING ANXIETY IN NON-HUMAN MAMMALS BY INCREASING BRAIN SEROTONIN LEVELS

(71) Applicant: Alain Martin, Flemington, NJ (US)

(72) Inventor: Alain Martin, Flemington, NJ (US)

(73) Assignee: NORTH CELL PHARMCETICALS INC., Flemington, NJ (US)

(*) Notice: Subject to any disclaimer, the term of this patent is extended or adjusted under 35 U.S.C. 154(b) by 308 days.

This patent is subject to a terminal disclaimer.

(21) Appl. No.: 16/873,190

(22) Filed: Feb. 25, 2020

(65) Prior Publication Data

US 2021/0260030 A1    Aug. 26, 2021

(51) Int. Cl.
| | | |
|---|---|---|
| *A61K 31/405* | (2006.01) | |
| *A61K 9/00* | (2006.01) | |
| *A61P 25/22* | (2006.01) | |
| *A61K 31/4045* | (2006.01) | |

(52) U.S. Cl.
CPC .......... *A61K 31/405* (2013.01); *A61K 9/0043* (2013.01); *A61K 9/0078* (2013.01); *A61K 31/4045* (2013.01); *A61P 25/22* (2018.01)

(58) Field of Classification Search
CPC .. A61K 31/4045; A61K 31/405; A61K 9/007; A61K 9/0073; A61K 9/0078
See application file for complete search history.

(56) References Cited

U.S. PATENT DOCUMENTS

| | | |
|---|---|---|
| 6,430,764 B1 | 8/2002 | Peters |
| 6,469,049 B1 | 10/2002 | Meyerhoff et al. |
| 9,308,208 B2 | 4/2016 | Wensley et al. |
| 9,383,348 B2 | 7/2016 | Repine |
| 10,449,213 B2 | 10/2019 | Bienkiewicz |
| 2003/0113393 A1 | 6/2003 | Babish et al. |

OTHER PUBLICATIONS

Chen et al. Pharmazie. Nov. 2004;59(11):859-63 (Year: 2004).*

* cited by examiner

*Primary Examiner* — Jeffrey S Lundgren
*Assistant Examiner* — William Y Lee

(57) ABSTRACT

A method of reducing anxiety in a non-human mammal by increasing brain serotonin levels, includes: down regulating in vivo levels of indigenous inflammatory cytokines in the nasal cavity of said non-human mammal by delivering an effective amount of an anti-inflammatory formula to said nasal cavity, which formula includes: at least one lipid-soluble antioxidant (which also functions as an anti-inflammatory agent) (the lipid-soluble antioxidant may be selected from the group consisting of alpha lipoic acid, aloe vera, omega 3 oil, N-acetylcysteine, cannabidiol, civet, oxytocin and combinations thereof); melatonin; tryptophan; and at least one essential oil. The most preferred antioxidant is N-acetylcysteine and the preferred essential oil is combination of chamomile, lavender and lemon oil.

19 Claims, No Drawings

METHOD OF REDUCING ANXIETY IN NON-HUMAN MAMMALS BY INCREASING BRAIN SEROTONIN LEVELS

REFERENCE TO RELATED APPLICATIONS

The present application has no related pending or abandoned or published prior patent applications or patents.

BACKGROUND OF INVENTION a. Field of Invention

The present invention relates to methods for treating anxiety in non-human mammals by increasing brain serotonin levels. The methods involve down regulating indigenous in vivo levels of inflammatory cytokines in the nasal cavity, which, when elevated, cause congestion, mucus, and diminish the effects of essential oils, tryptophan, and melatonin in the nasal cavity. The present invention methods utilize delivery of select formulae to the non-human mammal nasal cavity by any known liquid delivery mechanism, but especially nebulizers and sprayers. The select formulae include at least one antioxidant, at least one essential oil, tryptophan, and melatonin, delivered into the nasal cavity of the mammals to increase brain serotonin levels to decrease anxiety. These present invention methods may be used to decrease anxiety in most non-human mammals, such as, but not limited to, dogs and cats (pet or feral), as well as tame animals, cows, sheep, beef cattle, pigs, etc. and untamed animals, such as bears, lions, tigers, and other big cats, squirrels, coyotes, wolves, etc. These methods are particularly helpful regarding temporarily captured animals, such as city captured-country released wild animals, zoo animals, animals in heat, high strung pets and anxious pets. A most preferred antioxidant/anti-inflammatory agent is N-Acetyl-cysteine, and the essential oils are selected from chamomile, lavender and lemon oil, and especially combinations thereof, with the addition of melatonin and tryptophan, which is delivered, for example, by aerosol spray.

b. Prior Art Statement

The following references are of interest:

U.S. Pat. No. 6,430,764 discloses the use of a herbal scented pillow with essential oils for soothing and revitalizing the user.

U.S. Pat. No. 6,469,049 discloses a Method of treating, preventing or inhibiting central nervous system and diseases with the use of melatonin and N-acetylcysteine as a few of the oxygen radical scavengers listed delivered orally.

U.S. Pat. No. 9,308,208 discloses an Aerosol generating method and device to deliver various compounds.

U.S. Pat. No. 10,449,213 discloses a combinatorial approach to treating Alzheimer's disease with melatonin by transdermal delivery.

US Patent Application Publication No. 20030113393 discloses complex mixtures exhibiting selective inhibition of cyclooxygenase-2 with essential oils delivered topically or orally.

U.S. Pat. No. 9,383,348 Composition and methods for treating lung disorders, discloses the use of N-acetylcysteine to treat lung disorders.

While the above patents disclose the use of one or more compounds used in the formulae of the present invention methods, none of them provide novel methods for treating anxiety in non-human mammals, such as wild animals, dogs or other pets, by down regulating indigenous in vivo levels of inflammatory cytokines in the nasal cavity, which when elevated, cause congestion, mucus, and diminish the effect of essential oils, tryptophan, melatonin. In the present invention, it is achieved by increasing brain serotonin levels to decrease anxiety, wherein this method includes delivery of at least one anti-inflammatory agent, such as N-Acetylcysteine, and essential oils are selected from chamomile, lavender and lemon oil with the addition of melatonin and tryptophan, which can be delivered by aerosol spray.

SUMMARY OF INVENTION

The present invention relates to a method of reducing anxiety in a non-human mammal by increasing brain serotonin levels, which includes down regulating in vivo levels of indigenous inflammatory cytokines in the nasal cavity of said non-human mammal by delivering an effective amount of an anti-inflammatory formula to said nasal cavity, which formula includes: a) at least one lipid-soluble antioxidant; b) melatonin; c) tryptophan; and e) at least one essential oil. In some preferred embodiments, the at least one essential oil is selected from the group consisting of chamomile, lavender and lemon oil, and is most preferably a combination of chamomile, lavender and lemon oil. Water soluble antioxidants like vitamin C or N-acetylcysteine become lipid-soluble antioxidants when placed in the aqueous phase of an oil emulsion which disperses the water-soluble antioxidant equally in the oil phase.

In some embodiments of the present invention method, delivery is by a spray device selected from the group consisting of a nebulizer diffuser, an aerosol sprayer and a spray mechanism. In some embodiments, the formula includes a liquid carrier selected from the group consisting of aqueous, aqueous-oil and oil liquid carriers.

In some embodiments of the present invention method, the lipid-soluble antioxidant is selected from the group consisting of alpha lipoic acid, aloe vera, omega 3 oil, and combinations thereof. In other embodiments of the present invention method, the lipid-soluble antioxidant is selected from the group consisting of vitamin A, vitamin B, vitamin C, carotene, tocopherol, cannabidiol salts thereof and mixtures thereof. In some embodiments of the present invention method, the lipid-soluble antioxidant is a form of tocopherol selected from the group consisting of vitamin E, vitamin E esters, vitamin E salts, N-acetylcysteine and combinations thereof. In other embodiments of the present invention method, the lipid-soluble antioxidant is preferably selected from the group consisting of vitamin E, vitamin E acetate, sodium citrate, and N-acetylcysteine. In the most preferred embodiment, the water-soluble antioxidant is N-acetylcysteine delivered in an oil emulsion, which makes it a lipid soluble antioxidant.

In various embodiments of the present invention method, the antioxidant is within the range of about 0.1% to about 5% by weight of said formula and is preferably within the range of about 0.2% to about 2% by weight of said formula.

In various embodiments of the present invention method, the melatonin is within the range of about 0.1% to about 5% by weight of said formula and is preferably within the range of about 0.2% to about 2% by weight of said formula.

In various embodiments of the present invention method, the tryptophan is within the range of about 0.1% to about 5% by weight of said formula and is preferably within the range of about 0.2% to about 2% by weight of said formula.

In various embodiments of the present invention method, the cannabidiol is within the range of about 2% to about 20% by weight of said formula and is preferably within the range of about 5% to about 10% by weight of said formula.

In various embodiments of the present invention method, the at least one essential oil is within the range of about 65% to about 97.5% by weight of said formula and is preferably within the range of about 84% to about 94.5% by weight of said formula.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

DETAILED DESCRIPTION OF THE PRESENT INVENTION

Fear and anxiety in animals are common causes of a variety of behavioral disorders that affect the lives of these animals, such as wild and tamed animals, e.g., zoo animals, dogs, horses and other pets, as well as those who live and/or work with them. In most species, a physiological stress response occurs following exposure to a fear or anxiety-provoking stimulus. This stress response is thought to have both short and long-term effects on health and lifespan of the individual animal. An epidemiological survey of previous dog owners examines the long-term health and lifespan consequences of being a fearful or anxious dog. It is shown that certain fears and anxieties are prevalent in the domestic canine population and that there are prominent breed predispositions to particular behaviors that may have genetic components.

These observations carry over to horses, captured wild animals, etc. These tendencies towards fear and anxiety are associated with increased aggressions, as well as specific health and lifespan consequences, including an increased severity of other negative symptoms. For example, a frequency of skin disorders in dogs with non-social fear and separation anxiety and a shortened lifespan in those dogs that are more fearful of strangers are observed. To date no known treatment for anxiety in non-human exist that can be used to increase serotonin levels to reduce their anxiety.

Dogs selected for one study exhibited anxiety when their owners left for work. They exhibited a variety of this disorder, including aggression, urinating or defecating in the house, drooling, panting, destructive behavior, depression, excessive barking, and pacing.

The animal olfactory system contains the nasal cavity, olfactory epithelium, vomeronasal organ, and olfactory bulb. In dogs, for example, the nasal cavity has 3 nasal turbinates' that increase mucosal surface area. The olfactory epithelium has constantly regenerating olfactory receptor cells, each containing hundreds of cilia that facilitate superior odor detection; importantly, each olfactory receptor cell has only 1 type of olfactory receptor. A dog's sense of smell is 10,000 to 100,000 times greater than that of humans, likewise, to varying degrees for most other non-human mammals. This superior olfaction is especially important for working dogs, such as those that work in law enforcement and the military. However, little is currently known about how health, management, and the microbiota impact canine olfaction.

The vomeronasal organ detects nonvolatile odorants, such as pheromones, that influence social behavior. The olfactory bulb filters sensory input and communicates with the cerebral cortex. This communication underlies the importance of the memory of smell in working dogs, the durability of which can depend on training methods.

When an animal sniffs, air flows in the front and out the side of the nose, allowing for efficient air sampling. Each nostril intakes air separately, with sensory input going to the ipsilateral side of the brain (e.g., right nostril, right brain hemisphere). The right nostril sniffs conspecific and new odors and the left nostril sniffs familiar and non-aversive odors. Notably, olfactory receptors have been identified in the nasal cavity and GI tract and affect serotonin secretion; serotonin regulates olfactory information processing, suggesting a link between GI microbiota and olfaction. In addition, previous research has identified a link between nasal microbiota and olfactory performance. Anxiety increases nasal inflammatory cytokines, that increase nasal congestion and mucus, that decrease the calming effects of essential oils, with CBD oil, melatonin and tryptophan inhalants.

Inflammatory agents are produced by a wide variety of body cells and are natural proteins produced by the cells of the immune system of most vertebrates in response to challenges by foreign agents such as viruses, bacteria, parasites, and tumor cells and anxiety.

Cytokines are a group of proteins and peptides that are used in organisms as signaling compounds and are used to allow one cell to communicate with another. The cytokine family consists mainly of smaller water-soluble proteins and glycoproteins. Cytokines are released by many types of cells, principally activated lymphocytes, and macrophages but also endothelium, epithelium and connective tissue. They are particularly important in both innate and adaptive immune responses. Due to their central role in the immune system, cytokines are involved in a variety of immunological, inflammatory and infectious diseases. Interleukins (ILs) are a group of inflammatory cytokines that were first seen to be expressed by white blood cells. Interleukins are produced by a wide variety of bodily cells including endothelial cells and macrophages. The family of interleukins includes IL-1 to IL-33. The function of the immune system depends in a large part on interleukins, and rare deficiencies of a number of them have been described, all featuring autoimmune diseases or immune deficiency.

IL-8 is responsible in attracting white blood cells to the site of infection. The major cytokines that mediate inflammation are IL-1, IL-8, and TNF ($\alpha$ and $\beta$). IL-1 and TNF-$\alpha$ are produced by activated macrophages. Their secretion can be stimulated by infections, endotoxins, immune complexes, toxins, physical injury, anxiety, and a variety of inflammatory processes. Their most important actions in inflammation are their effect on endothelium, leukocytes, and fibroblasts and induction of the systemic acute phase reactions. IL-1, IL-8, and IL-6 also induce the systemic acute phase responses associated with infection, or injury, including fever, loss of appetite, the production of slow wave sleep, release of neutrophils into circulation, release of hormones, hemodynamic effects of septic shock, hypotension, anxiety, decrease in vascular resistance, increased heart rate, and decrease in blood pH.

Monocyte chemoattractant protein-1 (MCP-1/CCL2) is one of the key chemokines that regulate migration and infiltration of monocytes/macrophages. Both CCL2 and its receptor CCR2 have been demonstrated to be induced and involved in various diseases. Migration of monocytes from the blood stream across the vascular endothelium is required for routine immunological surveillance of tissues, as well as in response to inflammation.

The present invention provides novel methods for treating anxiety in non-human mammals, untamed animals and domesticated animals, by down regulating indigenous in vivo levels of inflammatory cytokines in the nasal cavity, which when elevated, causes congestion, mucus, and diminishes the effect of essential oils, tryptophan, melatonin and CBD oil in the nasal cavity, to increase brain serotonin levels, by delivery of select formulae to the nasal cavity by spay, such as aerosol spray or nebulization.

The term "pharmaceutically acceptable," such as pharmaceutically acceptable carriers, excipients, etc., refers to pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methane sulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique well known to pharmaceutical chemists to obtain improved physical and chemical stability, hygroscopicity, and solubility of compounds. See, e.g., H. Ansel et. al., Pharmaceutical Dosage Forms and Drug Delivery Systems ($6^{th}$ Ed. 1995) at pp. 196 and 1456-1457.

The term "prodrug" or "precursor" refers to compounds, which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bio-reversible derivatives are used interchangeably. By inference, latentiation implies a time lag element or time component involved in regenerating the bioactive parent molecule in vivo. The term prodrug is general in that it includes latentiated drug derivatives as well as those substances, which are converted after administration to the actual substance, which combines with receptors. The term prodrug is a generic term for agents, which undergo biotransformation prior to exhibiting their pharmacological actions.

The term "therapeutically effective amount" refers to an amount of a therapeutically effective compound, or a pharmaceutically acceptable salt thereof, which is effective to treat, prevent, alleviate or ameliorate symptoms of a disease.

Antioxidants

A key component of the formulae used in the present invention methods is antioxidants with anti-inflammatory effects to reduce nasal inflammatory cytokines. Antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention may be selected from the group consisting of all forms of N-acetylcysteine, vitamin A (retinol), all forms of vitamin B (3,4-didehydroretinol), all forms of carotene such as alpha-carotene, beta-carotene, gamma-carotene, sigma-carotene, all forms of vitamin C (D-ascorbic acid, L-ascorbic acid), all forms of tocopherol such as vitamin E (alpha-tocopherol, 3,4-dihydro-2,5,7,8-tetramethyl-2-(4,8,12-trimethyltri-decyl)-2H-1-benzop-yran-6-ol), (alpha-tocopherol, gamma-tocopherol, delta-tocopherol, tocoquinone, tocotrienol, and vitamin E esters which readily undergo hydrolysis to vitamin E such as vitamin E acetate and vitamin E succinate, and pharmaceutically acceptable vitamin E salts such as vitamin E phosphate, prodrugs of vitamin A, carotene, vitamin C, and vitamin E, pharmaceutically acceptable salts of vitamin A, carotene, vitamin C, .alpha.-lipoic acid and vitamin E, and the like, aloe vera, omega 3 oils, civet, and mixtures thereof. Preferably, the antioxidant is selected from the group of lipid-soluble antioxidants consisting of vitamin A, carotene, vitamin E, vitamin E acetate, and mixtures thereof. More preferably, the antioxidant is vitamin E or vitamin E acetate or N-acetylcysteine or mixtures thereof. Most preferably, the antioxidant is vitamin E acetate or N-acetylcysteine or mixtures thereof.

N-Acetylcysteine, a preferred choice antioxidant in the formulae of the present invention methods, can act as an anti-inflammatory mediator that neutralizes oxygen radicals directly, thus lowering the level of inflammatory cytokines and mucus in the nasal cavity. N-acetylcysteine (NAC) is a chemically modified form of the dietary amino acid cysteine. Both cysteine and NAC contain Sulphur, and Sulphur-containing amino acids function as antioxidants, protecting the body from damage by oxidation.

Applicant has discovered that lipid-soluble antioxidants, water soluble antioxidants such as N-acetylcysteine (NAC) delivered in an oil emulsion, in combination with essential oils, CBD oil melatonin and tryptophan acted synergistically to down regulate indigenous in vivo levels of inflammatory agents such as cytokines in the nasal cavity, and increase the efficacy of the essential oils, CBD oil and tryptophan and melatonin to increase brain serotonin levels to calm anxiety in non-human mammals.

Most NAC is not used as an antidote to acetaminophen, but rather to neutralize oxidants produced in a variety of diseases. Chronic inflammation produces significant numbers or reactive oxygen species. NAC is used to counter the damaging effects of inflammation, particularly where delicate and vital organs are being damaged. One example is the use of NAC to help prevent oxidative damage to the spinal cord in degenerative myelopathy in dogs. Some research suggests that NAC also helps prevent kidney damage from lack of blood flow in humans, and it may have potential in the treatment of chronic kidney failure in geriatric cats. It can even be speculated that cats are more vulnerable to chronic renal failure because of their lower antioxidant levels.

A surprising potential benefit of NAC is in the treatment of retrovirus infection such as HIV (Human Immunodeficiency Virus which can cause AIDS) in humans and FIV (Feline Immunodeficiency Virus) in cats. In humans, high levels of oxidants stimulate HIV replication while antioxidants such as glutathione prevent replication. Similar results were seen in a study of FIV in cats when NAC inhibited immune cell destruction and suppressed viral replication. A final potential application of NAC in small animals is the breakdown of mucus accumulation in the airways, especially in the nasal cavity. In studies in dogs, NAC chemically reacted with and broke the disulfide bonds that hold mucus together, resulting in improved clearing of mucus and reduced mucus accumulation. NAC may thus be a useful treatment of respiratory disease with heavy mucus production. N-acetylcysteine is used in veterinary medicine for the treatment of acetaminophen toxicity in cats and dogs. Other potential applications for NAC include the treatment of degenerative myelopathy, respiratory disease, chronic renal failure and feline immune deficiency virus (Hy).

The following is a discussion of various components of preferred formulae used in the present invention methods:

The antioxidants used herein may first be prepped in saline solution for mixing with other constituents. This is a hypertonic saline solution with N-acetylcysteine that can be used for the daily nasal hygiene, stabilizing the nasal secretions, decreasing mucus, and cytokines. It contributes to wash out nasal secretions in a natural way; Enhances the natural antioxidant defense; Reduces dryness and hydrates the surface of the nasal cavity; Protects and prevents the production of bacterial biofilm; Helps reduce symptoms resulting from environmental pollution; Decreases nasal mucus and inflammatory cytokines.

Example Ingredients: N-acetylcysteine (NAC) 1%; 0.9% Saline solution

Tryptophan

Tryptophan is an amino acid needed for normal growth in infants and for nitrogen balance in adults. It is an essential amino acid. This means your body cannot produce it, so you must get it from your diet. The body uses tryptophan to help make niacin, melatonin, and serotonin. Serotonin is thought to produce healthy sleep and a stable mood to reduce anxiety. Amino acids, including tryptophan, are used as building blocks in protein biosynthesis, and proteins are required to sustain life. Many animals (including humans) cannot synthesize tryptophan: they need to obtain it through their diet, making it an essential amino acid. Tryptophan is among the less common amino acids found in proteins, but it plays important structural or functional roles whenever it occurs. For instance, tryptophan and tyrosine residues play special roles in "anchoring" membrane proteins within the cell membrane. In addition, tryptophan functions as a biochemical precursor for the following compounds: Serotonin (a neurotransmitter), synthesized by tryptophan hydroxylase. Melatonin (a neurohormone) is in turn synthesized from serotonin, via N-acetyltransferase and 5-hydroxyindole-O-methyltransferase enzymes. An increase in serotonin in the brain, results in decreased anxiety and inhibition of panic attacks in humans and dogs and other mammals. The 5-hydroxyindoleacetic acid (5-HIAA) urine test is used to help diagnose and brain serotonin levels. It may be ordered by itself or along with a blood serotonin and/or chromogranin A level. 5-HIAA is the primary metabolite of serotonin that is excreted in the urine. Niacin, also known as vitamin $B_3$, is synthesized from tryptophan via kynurenine and quinolinic acids. Auxins (a class of phytohormones) are synthesized from tryptophan. In Dogs, a disorder called fructose malabsorption causes improper absorption of tryptophan in the intestine, reduced levels of tryptophan in the blood, and depression. For prep for mixing with other formulae constituents, Dissolve 1 mg of DL-tryptophan in 1 ml of distilled water (make a 1:10 dilution from the 1 mg/mL stock to get 0.1 mg/mL). Weigh 15-20 mg of fine powdered defatted flour and dissolve in water at 1 mg/mL. To date the delivery of Tryptophan has been given orally as a component of a diet. The inhalation of tryptophan is new and novel.

Melatonin

Melatonin produced by tryptophan is a hormone found naturally in the body. Melatonin is also taken by mouth for the inability to fall asleep (insomnia); delayed sleep phase syndrome (DSPS); rapid eye movement sleep behavior disorder (RBD); insomnia associated with attention deficit-hyperactivity disorder (ADHD); insomnia associated with traumatic brain injury (TBI); and sleep problems in children with developmental disorders including autism, cerebral palsy, and intellectual disabilities. It is also taken by mouth as a sleep aid after discontinuing the use of benzodiazepine drugs and to reduce the side effects of stopping smoking.

Essential Oils

Aromatherapy is a form of alternative medicine that uses natural oils to enhance psychological and physical well-being. This is now an important part of everyday life for many people, and some are even extending its use to their four-legged family members! Aromatherapy works via the senses, and in addition to the positive effect of touch that your dog will receive when you treat him with oils, he will benefit from their smell. Since your dog's nose is much more sensitive to smell than yours, it's not surprising that this form of holistic therapy is gaining popularity amongst pet owners. After being applied to the skin, the oils evaporate and are inhaled. Their aromatic molecules enter the nasal cavity, sinuses and lungs, and are then absorbed into the bloodstream. Essential oils are also considered to possess "vibrational energy"—this is supposed to have a positive healing effect on the emotional states of the body and mind. There are hundreds of essential oils available, all of which can have different effects on animals. And just as is the case in people, different dogs react differently to any one type of oil. Although many are used on animals, particularly pets, the most popular essential oils are lavender, lemon oil, chamomile oil and *eucalyptus.*

Lavender Oil and Lemon Oil

Lavender oil and lemon oil are considered to have a variety of benefits for pets, and is especially noted for the following properties: Calming, sedative action: It is an excellent oil to help calm dogs that are fearful, agitated, hyperactive or anxious. Flea and tick control: Although it doesn't kill fleas and ticks, it can be useful in helping to repel them. Skin therapy: It can help to provide some relief when applied to dry, itchy skin. Fragrance: In addition to its medicinal benefits, its fragrance makes for an effective way to control pet odor.

*Eucalyptus* Oil

*Eucalyptus* oil is also very widely used for its numerous benefits, and is especially noted for the following properties: Flea control: Like lavender, this can help to repel these parasites. Skin therapy: It can be useful to help soothe skin after insect bites, stings, and skin rashes. Antiseptic qualities: Its disinfectant properties can be useful for skin problems and also when cleaning bedding. Respiratory therapy: Its inhalant properties help to combat respiratory problems such as sinus infections and bronchitis. Fragrance: *Eucalyptus* can also be very effective against pet odor.

Chamomile

The main constituents of chamomile flowers are polyphenol compounds, including apigenin, quercetin, patulin, and luteolin. Essential oil components extracted from the flowers are terpenoids. Chamomile is under preliminary research for its potential anti-anxiety properties. Chemical compounds present within chamomile include numerous polyphenols which have unknown effects in humans.

CBD Oil

CBD, or cannabidiol, is a compound found in *cannabis* and hemp. It is essential to note that in most cases, CBD does not contain delta-9-tetrahydrocannabinol (THC), the compound that gives marijuana its psychoactive properties. In fact, most CBD products are derived from hemp and not from marijuana. Currently, there has been no formal study on how CBD affects dogs. What scientists do know is that cannabinoids interact with the endocannabinoid receptors located in the central and peripheral nervous systems, which help maintain balance in the body and keep it in a normal healthy state. While there is no definitive scientific data on using CBD to treat dogs, there's anecdotal evidence from dog owners suggesting it can treat pain, especially neuropathic pain, as well as helping to control seizures.

CBD is also used because of its anti-inflammatory properties, cardiac benefits, anti-nausea effects, appetite stimulation, anti-anxiety impact, and for possible anti-cancer benefits, although there's no conclusive data on this use. While there's no scientific data on the side effects of CBD usage for dogs, there are potential side effects based on how CDB affects humans. Dry mouth, lower blood pressure and drowsiness all used to treat anxiety Pheromones: Cats love civetone a pheromone secreted by mammals called civet. It is used in the manufacture of perfumes which is why zoo animals love it.

Uses of Oxytocin

Studies in laboratory animals and humans suggest that the "love hormone" plays an important role in the establishment of social relationships and behaviors, such as caregiving. Oxytocin also may have anxiolytic properties, meaning it may help reduce anxiety. Oxytocin has been promoted as a "wonder drug" that can help enhance positive feelings and social skills while also purportedly alleviating serious cognitive and psychiatric and behavioral conditions, including depression, post-traumatic stress disorder (PTSD), in both humans and animals.

Nasal Inflammatory Agents

The inflammatory agents that may be treated by the present invention methods may be selected from a wide variety of inflammatory agents. Preferred cytokines may be selected from the group consisting of interleukin-1, interleukin-2, interleukin-4, interleukin-6, interleukin-8, interleukin-10, interleukin-17, and interleukin-23. More preferred cytokines are interleukin-1, interleukin-6, and interleukin-8. IL-10, IL-17, and IL-23 are all regulated by the levels of IL-6 and IL-8 and so regulation of IL-6 and IL-8 can regulate IL-10, IL-17, IL-23 and MCP-1.

The compounds of the formulae used in the present invention methods can be prepared according to the examples set out below. The examples are presented for purposes of demonstrating, but not limiting, the preparation of the compounds and compositions and the methods of use in accordance with this invention.

Formula Delivery

Using a duel nasal spray chambered delivery system, place the water-soluble components into one chamber, 1% N acetylcysteine in physiological saline and 0.1 mg/mL tryptophan are in one chamber. In the other chamber add equal parts of the essential oils, chamomile oil, lavender oil, lemon oil, melatonin and CBD oil. Another method of aerosolizing the formulas is to put the ingredients into an essential oil nebulizing diffuser that is used in aromatherapy. Alternatively, all constituents may be mixed and delivered by aerosol spray, such as with bag-on-valve sprayers.

EXAMPLES

A present invention method for treating large zoo animals to reduce anxiety and aggression involve remotely activated sprayer delivery to the nasal cavity of a formula selected from Examples 1 through 8. The sprayer may be located above a food tray inside night cages:

Example 1

All by weight: 2% lipid-soluble antioxidant mixture of emulsion mixture of N-acetylcysteine; 3% melatonin; 10% cannabidiol; 2% tryptophan; and balance equal parts essential oils: chamomile and lemon oil.

Example 2

All by weight: 1.5% lipid-soluble antioxidant mixture of vitamin E, vitamin E ester; 3% melatonin; 1% tryptophan; and balance equal parts essential oils: chamomile, lavender and lemon oil.

Example 3

All by weight: 1.5% lipid-soluble antioxidant emulsion mixture of N-acetylcysteine, 3% melatonin; 1% tryptophan; and balance equal parts essential oils: chamomile, *eucalyptus* and lemon oil.

Example 4

All by weight: 0.5% lipid-soluble antioxidant mixture of tocoquinone, vitamin C and vitamin E ester; 1% melatonin; 8% cannabidiol; 1% tryptophan; and balance equal parts essential oils: lavender and lemon oil.

Example 5

All by weight: 0.3% lipid-soluble antioxidant mixture of omega 3 oils and N-acetylcysteine emulsion, vitamin E ester; 3% melatonin; 1% tryptophan; and balance equal parts essential oils: chamomile, *eucalyptus* and lemon oil.

Example 6

All by weight: 2.3% lipid-soluble antioxidant mixture of aloe vera, omega 3 oils and N-acetylcysteine; 2% melatonin; 18% cannabidiol; 1% tryptophan; and balance equal parts essential oils: chamomile, lavender and lemon oil.

Example 7

All by weight: 2.3% lipid-soluble antioxidant mixture of aloe vera, civet and N-acetylcysteine; 2% melatonin; 1% tryptophan; and balance equal parts essential oils: chamomile, lavender and lemon oil.

Example 8

All by weight: 2.3% lipid-soluble antioxidant mixture of aloe vera, oxytocin and N-acetylcysteine; 2% melatonin; 1% tryptophan; and balance equal parts essential oils: chamomile, lavender and lemon oil.

Example 9—Inhaled Formula for the Treatment of Anxiety in Dogs (Double Blind, Placebo-Controlled, Safety Study, Nasal Inflammatory Biomarkers)

All dogs enrolled that were dosed using a nasal mist, or aroma therapy with plug in aroma units, were able to provide nasal samples for analysis before and after nasal exposure to the formulation containing _1_N-acetylcysteine, _1%_tryptophan, _2%_melatonin, and _96_% three essential oils (equal parts chamomile, lavender, lemon oil). Specimens were of good quality for the planned assays. Samples were sent for processing. The aliquot was treated with protease inhibitors pheylmethanesulfonyl fluoride (PMSF) and ethylenediamine tetra acetic acid (EDTA) to stop any degradation of the cytokines of interest (IL-6, IL-8, and MCP-1. For IL-10, IL-17 and IL-23, levels were at or below the limit of detection for the assays (7, 2 and 20 pg/mL respectively). For the other markers (IL-6, IL-8, MCP-1) levels detected where within those typically found in the nasal cavity of dogs. Overall, significant changes were noted in these biomarkers tested for the group as a whole (Tables 1-3).

TABLE 1

Average of IL-6 in both nasal cavities of dogs that were measured then treated with the anti-anxiety Therapy (drug)

| | | |
|---|---|---|
| Pre Drug | 434 pgm/mL | 90.9 pgm/mL |
| Post Drug | 245 pgm/mL | 31.1 pgm/mL |
| Differences in IL-6 "Post-Drug" minus "Pre-Drug" | −43% | −65% |

Table 1 illustrates median change from pre- to post-study drug inhalation in the nasal cavity of IL-6 levels before and after the anti-anxiety treatment by inhalation.

TABLE 2

Average of IL-8 in both nasal cavities of dogs that were measured then treated with the anti-anxiety Therapy (drug)

| | | |
|---|---|---|
| Pre Drug | 317.8 pgm/mL | 367 pgm/mL |
| Post Drug | 156.6 pgm/mL | 78 pgm/mL |
| Differences in IL-8 "Post-Drug" minus "Pre-Drug" | −51% | −79% |

Table 2 illustrates median change from pre- to post-study drug inhalation in the nasal cavity of IL-8 levels before and after the anti-anxiety treatment by inhalation.

TABLE 3

Average of MCP-1 in both nasal cavities of dogs that were measured, then treated with present invention anti-anxiety therapy (using sprayer drug delivery)

| | | |
|---|---|---|
| Pre Drug | 18.5 pgm/mL | 17.2 pgm/mL |
| Post Drug | 9.7 pgm/mL | 7.0 pgm/mL |
| Differences in MCP-1 "Post-Drug" minus "Pre-Drug" | −48% | −60% |

Table 3 illustrates median change from pre- to post-study drug inhalation in the nasal cavity of MCP-1 levels before and after anti-anxiety treatment by inhalation.

The data clearly showed that this formula down regulated inflammation and inflammatory cytokines in the nasal cavity to allow the essential oils (chamomile, lavender, lemon oil), melatonin and tryptophan to decrease anxiety in dogs. CBD oil can also be added that slightly enhanced the formulas effect.

Example 10

Assessment of dog behavior by owner after the use of the aerosol spray for five days. The owners recorded each behavior daily and provided the numbers to determine the decrease in anxiety in the animal. The product was rated by the owners 1-10 with 1 being negative and 10 being great. NA means not applicable; the dog did not exhibit that behavior.

TABLE 4

| Dog owners | Percentage decrease in urination | Percentage decrease in defecating | Percentage decrease in panting | Percentage decrease in barking | Percentage decrease in excessive chewing | Overall Rating of product 1-10 |
|---|---|---|---|---|---|---|
| 1 | 71% | NA | 52% | 56% | NA | 8 |
| 2 | NA | 100% | 64% | 63% | NA | 9 |
| 3 | 90% | NA | NA | NA | 90% | 9 |
| 4 | NA | NA | NA | 76% | NA | 10 |
| 5 | NA | 100% | 83% | 68% | NA | 9 |
| 6 | 100% | 80% | NA | NA | 75% | 10 |
| 7 | NA | NA | NA | NA | 65% | 6 |
| 8 | NA | NA | 92% | 90% | 56% | 9 |
| 8 | 100% | 90% | NA | 63% | NA | 8 |
| 10 | 100% | 100% | NA | 100% | NA | 8 |

The data clearly showed that this formula down regulated inflammation and inflammatory cytokines in the nasal cavity with N-acetylcysteine to allow the essential oils (chamomile, lavender, lemon oil), melatonin and tryptophan to decrease the symptoms of anxiety in dogs.

Example 11

The data from the other dogs tested were first used to test combinations of the new formula. Five dogs with urination anxiety problems were tested for two days on each formula below. The percentage of decrease in daily in house urination was recorded. The number of urination events was averaged over those two days of testing for each formula. N-acetylcysteine and tryptophan in one chamber and the essential oils (chamomile, lavender, lemon oil), melatonin in the other chamber is given nasally in the aerosol spray. This same synergistic treatment worked on cats and other pets. This formula can also be delivered in an aerosol mist vaporizer. CBD oil can also be added if needed.

TABLE 5

Percentage decrease in anxiety as measured by inhouse urination

| | |
|---|---|
| Essential oils | 21% |
| Essential oils with tryptophan | 22% |
| Essential oils with N-acetylcysteine | 20% |
| Essential oils with melatonin | 23% |
| Essential oils Tryptophan and N-acetylcysteine | 30% |
| Essential oils with tryptophan and melatonin | 35% |
| Essential oils with, N-acetylcysteine and melatonin | 39% |
| Essential oils, melatonin and N-acetylcysteine and tryptophan | 90% |
| Essential oils, melatonin and N-acetylcysteine and tryptophan CBD oil | 92% |
| Essential oils, melatonin and N-acetylcysteine and tryptophan Civet and or Oxytocin | 95% |

The data clearly showed that this formula down regulated inflammation and inflammatory cytokines in the nasal cavity with N-acetylcysteine to allow the essential oils (chamomile, lavender, lemon oil), melatonin and tryptophan to decrease the symptoms of anxiety in dogs.

Example 12 Serotonin Urine Tests

Urine samples were collected from the dogs and averaged for all formula listed above. The 5-hydroxyindoleacetic acid (5-HIAA) urine test is used to help diagnose and monitor serotonin levels. It may be ordered by itself or along with a blood serotonin and/or chromogranin A level. 5-HIAA is the primary metabolite of serotonin that is excreted in the urine. The only formula tested and listed above to increase serotonin levels over 64% was Essential oils (chamomile, lavender, lemon oil), melatonin and N-acetylcysteine, and Tryptophan. It increased serotonin over 64% over base line measurements. It appears that adding CBD oil may have some added effect.

TABLE 6

Percentage increase in Serotonin

| | |
|---|---|
| Essential oils | 8% |
| Essential oils with tryptophan | 9% |
| Essential oils with N-acetylcysteine | 8% |
| Essential oils with melatonin | 18% |
| Essential oils Tryptophan and N-acetylcysteine | 11% |
| Essential oils with tryptophan and melatonin | 19% |
| Essential oils with, N-acetylcysteine and melatonin | 17% |
| Essential oils, melatonin and N-acetylcysteine and tryptophan | 64% |
| Essential oils, melatonin and N-acetylcysteine and tryptophan CBD oil or Civet | 65% |
| Essential oils, melatonin and N-acetylcysteine and tryptophan Oxytocin and or Civet | 69% |

The same results were achieved with the use of another anti-inflammatory, antioxidant agent in place of N-acetylcysteine with the use of Vitamin E, omega 3 oils, and lipid soluble antioxidants.

Examples 13 Through 16

The same results were achieved with the use of another anti-inflammatory, antioxidant agent in place of N-acetylcysteine with the use of Vitamin E, omega 3 oils, and lipid soluble antioxidants.

Example 17

A wild bear enters an urban area, scaring residents and overturning trash cans. The game warden arrives, anesthetizes the bear and removes it to a mobile cage trailer for transportation to a distant wooded release area. The warden knows that the bear will awake in a very anxious and dangerous state before it is released. After caging the bear, a present invention formula is sprayed into the nasal cavities before the bear wakes up, to decrease the anxiety and potential danger to humans when it does wake up and is released. The following formula is suggested: All by weight: 3% lipid-soluble antioxidant (mixture of ¼ aloe vera, ½ omega 3 oils and ¼ N-acetylcysteine); 3% melatonin; 18% cannabidiol; 3% tryptophan; and balance equal parts essential oils: chamomile, lavender and lemon oil. On wild animals CBD oil may have some positive effects, not found in domesticated animals.

Example 18

When the pet owners used the aerosolized formulas in an essential oil nebulizing diffuser that is used in aromatherapy with melatonin, tryptophan, and N acetylcysteine, or in a nasal spray, the aerosolized formula calmed the pets down and relieved anxiety in the pets that helped them sleep better all night. Because a dog has 10,000 times to 100,000 times the sensitivity to this formula, the formula only affected the pets and not the human owners. The owners reported that the vaporizer formula produced a pleasant odor with a calming effect.

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example. Obviously, numerous modifications and variations of the present invention are possible in the light of the above teachings and the invention is not limited to the examples herein. It is therefore understood that within the scope of the appended claims, the invention may be practiced otherwise than as specifically described herein.

What is claimed is:

1. A method of reducing anxiety in a non-human mammal by increasing brain serotonin levels, which comprises:
   down regulating in vivo levels of indigenous inflammatory cytokines in the nasal cavity of said non-human mammal by delivering an effective amount of an anti-inflammatory formula to said nasal cavity, which formula includes:
   a) at least one antioxidant that is selected from water-soluble antioxidants, lipid-soluble antioxidants and both;
   b) melatonin;
   c) tryptophan; and
   d) at least one essential oil;
   wherein said delivering is delivery by a spray device selected from the group consisting of a nebulizer diffuser, an aerosol sprayer and a spray mechanism.

2. The method of claim 1 wherein said at least one essential oil is selected from the group consisting of chamomile, lavender and lemon oil.

3. The method of claim 1 wherein said at least one essential oil is a combination of chamomile, lavender and lemon oil.

4. The method of claim 1 wherein said formula includes a liquid carrier selected from the group consisting of aqueous, aqueous-oil and oil liquid carriers.

5. The method of claim 1 wherein said antioxidant is selected from the group consisting of alpha lipoic acid, aloe vera, omega 3 oil, cannabidiol, civet, oxytocin and combinations thereof.

6. The method of claim 1 wherein said antioxidant is selected from the group consisting of vitamin A, vitamin B, vitamin C, carotene, tocopherol, salts thereof and mixtures thereof.

7. The method of claim 1 wherein said antioxidant is a form of tocopherol selected from the group consisting of vitamin E, vitamin E esters, vitamin E salts, N-acetylcysteine and combinations thereof.

8. The method of claim 1 wherein said antioxidant is selected from the group consisting of vitamin E, vitamin E acetate and N-acetylcysteine.

9. The method of claim 8 wherein said antioxidant is N-acetylcysteine in an emulsion.

10. The method of claim 1 wherein said antioxidant is within the range of about 0.1% to about 5% by weight of said formula.

11. The method of claim 1 wherein said antioxidant is within the range of about 0.2% to about 2% by weight of said formula.

12. The method of claim 1 wherein said melatonin is within the range of about 0.1% to about 5% by weight of said formula.

13. The method of claim 1 wherein said melatonin is within the range of about 0.2% to about 2% by weight of said formula.

14. The method of claim 1 wherein said tryptophan is within the range of about 0.1% to about 5% by weight of said formula.

15. The method of claim 1 wherein said tryptophan is within the range of about 0.2% to about 2% by weight of said formula.

16. The method of claim 1 wherein said cannabidiol is within the range of about 2% to about 20% by weight of said formula.

17. The method of claim 1 wherein said cannabidiol is within the range of about 5% to about 10% by weight of said formula.

18. The method of claim 1 wherein said at least one essential oil is within the range of about 65% to about 97.5% by weight of said formula.

19. The method of claim 1 wherein said at least one essential oil is within the range of about 84% to about 94.5% by weight of said formula.

* * * * *